(12) United States Patent
Saur et al.

(10) Patent No.: US 11,416,699 B2
(45) Date of Patent: Aug. 16, 2022

(54) MACHINE LEARNING SYSTEM FOR IDENTIFYING A STATE OF A SURGERY, AND ASSISTANCE FUNCTION

(71) Applicant: Carl Zeiss Meditec AG, Jena (DE)

(72) Inventors: Stefan Saur, Aalen (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 135 days.

(21) Appl. No.: 17/197,773

(22) Filed: Mar. 10, 2021

(65) Prior Publication Data

US 2021/0286996 A1    Sep. 16, 2021

(51) Int. Cl.
| | | |
|---|---|---|
| *G06K 9/00* | (2006.01) | |
| *G06K 9/62* | (2022.01) | |
| *G16H 30/20* | (2018.01) | |
| *G16H 20/40* | (2018.01) | |
| *G06N 20/00* | (2019.01) | |

(52) U.S. Cl.
CPC ....... *G06K 9/00624* (2013.01); *G06K 9/6256* (2013.01); *G06N 20/00* (2019.01); *G16H 20/40* (2018.01); *G16H 30/20* (2018.01)

(58) Field of Classification Search
CPC .. G06K 9/00624; G06K 9/6256; G16H 20/40; G16H 30/20; G06N 20/00
See application file for complete search history.

(56) References Cited

U.S. PATENT DOCUMENTS

| | | | |
|---|---|---|---|
| 5,733,256 A | | 3/1998 | Costin |
| 8,622,951 B2 * | | 1/2014 | Claus ..................... A61B 90/20 |
| | | | 604/22 |
| 2013/0226072 A1 * | 8/2013 | Kraus .................. A61F 9/00745 |
| | | | 604/22 |
| 2015/0077528 A1 * | 3/2015 | Awdeh ..................... A61B 3/14 |
| | | | 348/53 |
| 2016/0346123 A1 * | 12/2016 | Koplin ................... A61M 1/774 |
| 2017/0238798 A1 * | 8/2017 | Isogai .................. A61B 3/0008 |

FOREIGN PATENT DOCUMENTS

EP    2296596 B1    1/2017

OTHER PUBLICATIONS

Examination Report, Application No. DE 102020106607.4, dated Jan. 4, 2021, 12 pages.
Examination Report With English Translation, Application No. DE 102020106607.4, dated Jan. 4, 2021, 24 pages.

* cited by examiner

*Primary Examiner* — Tom Y Lu
(74) *Attorney, Agent, or Firm* — Honigman LLP; Brett A. Krueger

(57) ABSTRACT

A method and a system for generating an assistance function for an ophthalmological surgery are presented. The method includes capturing digital image data of a surgical microscope, which were generated during an ophthalmological surgery by an image sensor and which are annotated. The method furthermore includes capturing sensor data of a phaco system, which were generated during the ophthalmological surgery by a sensor of the phaco system and which are annotated, wherein the annotated sensor data and the annotated digital image data have synchronized timestamps and wherein the annotations refer in indicative fashion to a state of an ophthalmological surgery. Finally, the method includes training a first machine learning system by means of the annotated image data and the annotated sensor data to generate a learning model to predict a state of an ophthalmological surgery and, on the basis thereof, output a control signal, wherein the control signal is suitable for facilitating an assistance function in a subsequent use of the trained learning model during a prediction phase of a machine learning system.

16 Claims, 7 Drawing Sheets

100

102 Capturing digital image data of a surgical microscope

104 Capturing sensor data of a phaco system

106 Annotating the digital image data and the sensor data

108 Training a first machine learning system

| 202 | Capturing digital image data of a surgical microscope during an ophthalmological surgery |

| 204 | Capturing sensor data of a phaco system during the ophthalmological surgery |

| 206 | Determining a state of an ophthalmological surgery by means of a second machine learning system |

| 208 | Outputting the control signal |

| 210 | Controlling the assistance function by the control signal |

FIG. 2

MACHINE LEARNING SYSTEM FOR IDENTIFYING A STATE OF A SURGERY, AND ASSISTANCE FUNCTION

FIELD OF THE INVENTION

The invention relates to an assistance system for an ophthalmological surgery and, in particular, to an assistance system which identifies a state of the ophthalmological surgery and outputs a control signal. Moreover, the invention relates to a corresponding system and a corresponding computer program product for carrying out the method.

TECHNICAL BACKGROUND

In addition to other types of eye surgery, replacing the biological lens of an eye with an artificial intraocular lens (IOL)—for example, in the case of an (age-related) refractive error or in the case of cataracts—has become ever more common in the field of ophthalmology in recent years. In the process, the biological lens is detached from the capsular bag by way of a minimally invasive intervention and removed. The lens, which has become opacified in the case of a cataract, is then replaced by an artificial lens implant. In the process, this artificial lens implant, or intraocular lens, is inserted into the then empty capsular bag. Knowledge of the correct position of the intraocular lens and the necessary refractive power depend on one another.

Physicians are assisted by highly developed systems for these surgeries. Examples of such highly developed systems include surgical microscopes, phaco systems and, in part, robot systems and OCT (optical coherence tomography) systems, which are usable during the surgery. These systems generate a whole array of sensor data during the surgery; however, up until now, these could practically not, or only to a very limited extent, be made usable for future operations. Moreover, an interaction or a joint and coordinated use of the measurement data, generated thus, during the surgery is currently not envisaged.

Proceeding from these disadvantages of the known methods and assistance systems in ophthalmological surgeries, an underlying object of the concept presented herein consists of presenting a method and a system for an improved, integrated, and quickly usable assistance function for ophthalmological surgeries.

OVERVIEW OF THE INVENTION

This object is achieved by the method proposed here, the corresponding system and the associated computer program product as per the independent claims. Further embodiments are described by the respective dependent claims.

According to one aspect of the present invention, a computer-implemented method for generating an assistance function for an ophthalmological surgery is presented. The method can include capturing digital image data of a surgical microscope, which were generated during an ophthalmological surgery by an image sensor and which are annotated, and capturing sensor data of a phaco system, which were generated by a sensor of the phaco system during the ophthalmological surgery and which are annotated. Here, the annotated sensor data and the annotated digital image data can have synchronized timestamps and the annotations can be indicative for a state of an ophthalmological surgery.

Furthermore, the method can include training a first machine learning system by means of the annotated image data and the annotated sensor data to generate a learning model to predict a state of an ophthalmological surgery and, on the basis thereof, output a control signal. Here, the control signal can be suitable for facilitating an assistance function in a subsequent use of the trained learning model during a prediction phase of a machine learning system.

According to one aspect of the present invention, a method for using a learning model for predicting a state of an ophthalmological surgery is presented. The method can include capturing digital image data of a surgical microscope during an ophthalmological surgery and capturing sensor data of a phaco system during the ophthalmological surgery.

Additionally, this method can include determining a state of an ophthalmological surgery by means of a second machine learning system which has a trained learning model that is adapted to predict a state of an ophthalmological surgery; on the basis of the prediction of the state, the method can provide for the output of a control signal. Moreover, the method can include controlling an assistance function by the control signal during a prediction phase of the second machine learning system during the ophthalmological surgery.

According to a further aspect of the present invention, a first machine learning system for generating an assistance function for an ophthalmological surgery is presented. This system can comprise a storage unit for storing digital image data of a surgical microscope, which were generated during an ophthalmological surgery by an image sensor and which are annotated. Here, the storage unit can also be adapted to store sensor data of a phaco system, which were generated during the ophthalmological surgery by a sensor of the phaco system and which are annotated, wherein the annotated sensor data and the annotated digital image data have synchronized timestamps and wherein the annotations can refer to states of the ophthalmological surgery.

Moreover, provision can be made of a data processing installation, which comprises the storage unit, which is connected to a processor, and a training module, which is connected to the processor. This can be adapted, together with the processor, to train the first machine learning system by means of the annotated image data and the annotated sensor data to generate a learning model to predict a state of the ophthalmological surgery and, on the basis thereof, output a control signal. Here, the control signal can be suitable for facilitating an assistance function in a subsequent use of the machine learning model during a prediction phase of a machine learning system.

According to a fourth aspect of the present invention, a surgery assistance system for using a learning model for predicting a state of an ophthalmological surgery and, on the basis thereof, outputting a control signal is presented. To this end, the surgery assistance system can comprise a first capture module for capturing digital image data of a surgical microscope during an ophthalmological surgery, wherein the first capture module and the surgical microscope can be electrically interconnected for signal interchange.

The surgery assistance system can furthermore comprise a second capture module for capturing sensor data of a phaco system during the ophthalmological surgery, wherein the second capture module and the phaco system can be electrically connected to a data processing system for signal interchange. To this end, the capture modules can be electrically interconnected to the sensors for data interchange.

Additionally, provision can be made of a prediction module of a second machine learning system for a prediction of a state of the ophthalmological surgery, having a trained learning model which is adapted by preceding training to predict a state of an ophthalmological surgery and, on the basis of the prediction of the state, adapted to output a control signal.

This control signal in turn can be used as an input signal for a control module, which input signal is used by the control module during a prediction phase of the second machine learning system and during the ophthalmological surgery to control a parameter of a device used during the ophthalmological surgery.

Moreover, embodiments may relate to a computer program product able to be accessed from a computer-usable or computer-readable medium that contains program code for use by or in connection with a computer or any other instruction execution system. In the context of this description, a computer-usable or computer-readable medium can be any apparatus that is suitable for storing, communicating, transmitting, or transporting the program code.

The computer-implemented method for generating an assistance function for an ophthalmological surgery can have a plurality of advantages and technical effects which may also apply accordingly to the associated system:

Surgeons consider assistance functions a welcome aid—both in ophthalmology and in other types of surgical interventions—for making interventions safer. The concept proposed here makes a surgery device-overarching assistance function available. Here, it is not only sensor data (which also include image data) of one device that are resorted to but instead sensor data from more than one device are taken into account. Consequently, the learning model derived therefrom can take account of correlations not only of sensor data within one device; instead, use is made of the interaction and the integrated use of different functions and states of the devices. This facilitates a surgery device-overarching state identification, in particular of a phase of the respective surgery—this is a function which could not be realized previously since the device sensor data were not evaluated together in order to create (i.e., train) a learning model for a machine learning system from data of past surgeries.

Using the newly presented concept, it is possible to generate at least one control signal from the state identification of the surgery such that the surgery devices, in their interplay, assist the surgeon during the surgery. This reliably avoids possibly contradictory individual optimizations of the devices. Consequently, the surgeon receives an assistance function which—depending on the phase of surgery within the scope of an ophthalmological surgery—may extend to a live OCT system (or intraoperative OCT system), a surgical microscope, a robot system (which may be part of the surgical microscope) and a phaco system. Additionally, it is also possible to generate a plurality of control signals simultaneously and in coordinated fashion if a certain state of the surgery, and hence a certain phase, is identified. Then—depending on sensor input data—the machine learning system generates control signals which are appropriately matched to one another and which may directly relate to a plurality of devices.

In this way, it is possible to achieve advantages such as—in the case of an ophthalmological surgery—a reduction of the phaco energy, the capture of the lens elements, good section performance and increased chamber stability for fast, safe, and effective surgeries. It is possible to control both a switch between a peristaltic pump and the Venturi pump in a phaco system, and altered illumination conditions as a result of an increase or reduction in the radiation density of the microscope.

By way of example, if retinal bleeding is identified by the machine learning system on the basis of the image sensor data, maximum irrigation can automatically be activated by way of the control signal. Moreover, color temperatures of the illumination systems of a phaco system can be adapted by way of the control signal.

An option for displaying the identified state of the surgery by the machine learning system in the eyepiece not only facilitates an automatic generation of the control signal but also an option for the surgeon. They could confirm the generated control signal or reject the latter and would consequently remain in control of the surgery even in difficult situations. This further increases the surgical precision and facilitates an "expert in the box" function.

Here, some assistance functions are only rendered possible by an interaction if sensor data from both the microscope and the phaco system are present and can be used as input data for the machine learning system. By way of example, for improved control of the intraocular pressure, image-based data of the microscope, e.g., of the cornea, are also used in addition to the phaco system sensor data for irrigation and aspiration as input data for the machine learning system so as to identify a collapsing eye in an early stage and generate an appropriate control signal which, for example, may also trigger an alert for the surgeon or which is able to adapt the irrigation and/or aspiration parameters.

In the case of a surgery phase identification, which is restricted to image identification, for an assistance function in the phacoemulsification phase, it is necessary to identify the phaco tip on the basis of images. This may lead to errors. In contrast thereto, the concept proposed here allows, under simultaneous addition of the sensor data of the phaco system, a precise, unique selection of the control signal—and hence of the assistance function—on the basis of the trained behavior of the use phases of the phaco system, and hence said use need not be identified indirectly by way of the image analysis. This increases surgery safety and hence also the efficiency of the surgeon.

Further exemplary embodiments are presented below, which can be advantageous both in conjunction with the method and in conjunction with the corresponding system.

According to an advantageous exemplary embodiment, the method can include capturing sensor data and/or image data of a surgery robot, wherein the sensor data and/or image data were generated during the ophthalmological surgery and are annotated. Further, the method can include using the annotated sensor data and/or image data of the surgery robot during the training to generate the learning model. Moreover, use can be made of an array of further sensor data which can be used together with the image data and sensor data already discussed for the purposes of creating the learning model. Examples include sensor data of the surgical microscope such as zoom, focus settings, and light intensity settings and additional axis position data in the case of a robotic, motorized surgical microscope.

Moreover, rotation sensors might additionally be present if the displacement does not only have to be linear in the x-, y- or z-direction. These can then supply rotation-dependent sensor data. This would be helpful, for example, in the case of brain surgery, where neuro surgical microscopes are used since surgical accesses have to be flexibly adjustable in such cases.

Moreover, OCT image data of an OCT scanner and/or of a surgery robot can be captured in accordance with a further exemplary embodiment of the method. The OCT image data and/or the axis position data could also have been generated during the ophthalmological surgery and could moreover have been annotated. These data can also be used as additional training data. In principle, there is a restriction during the use of training data—they need to originate from the surroundings of true past operations.

According to a supplementary advantageous exemplary embodiment of the method, the determination of the state of the ophthalmological surgery can be based on a determination of a surgical instrument characteristic for the respective phase of surgery by applying the machine learning system. In this case, the machine learning system may have been trained specifically in respect of the digitally recorded images of the surgical microscope and the surgical instrument detectable therein. A sequence of surgical instruments can also be detected. By way of example, the use of a phaco system is only sensible following the use of an OCT system. And the insertion of an intraocular lens is only sensible following the use of the phaco system. Such rules can be used as additional boundary conditions when training the machine learning system. This can design the use of the learning model in a surgical phase to be more reliable.

According to one developed exemplary embodiment of the method, the control signal can be able to be used to control at least one parameter of devices that are used during the ophthalmological surgery. In this respect, a number of options are possible: controlling the light intensity of surgery lighting, acoustic or optical warnings in order to draw the attention to peculiarities during the surgery (e.g., incorrect manual settings of device parameters), zoom setting, focus setting and/or x/y-position setting, pressure setting in the phaco system for irrigation and aspiration, pulse shape setting of the phaco system, ultrasonic energy setting of the phaco system, activation state of the ultrasound on the phaco system to name but a few examples. If surgery robots are used, it is also possible to control rotation settings of the degree of freedom-controlling actuators of the surgery robot.

According to a further supplementary exemplary embodiment of the method, the captured digital image data and sensor data can be captured in time-synchronized fashion in a joint storage system. Here, time-synchronized means that they are each provided with a timestamp, are consequently available in a time series, and can be assigned to one another by way of the temporal dependence.

OVERVIEW OF THE FIGURES

It is pointed out that exemplary embodiments of the invention may be described with reference to different implementation categories. Some examples are in particular described with reference to a method, whereas other exemplary embodiments may be described in the context of corresponding apparatuses. Regardless of this, it is possible for a person skilled in the art to identify and to combine possible combinations of the features of the method and also possible combinations of features with the corresponding system from the description above and below—if not specified otherwise—even if these belong to different claims categories.

Aspects already described above and additional aspects of the present invention become apparent inter alia from the exemplary embodiments that are described and from the additional further specific refinements described with reference to the figures.

Preferred exemplary embodiments of the present invention are described below by way of example and with reference to the following figures:

FIG. 1 illustrates a flowchart-like representation of an exemplary embodiment of the computer-implemented method for generating an assistance function for an ophthalmological surgery.

FIG. 2 illustrates a flowchart-like representation of an exemplary embodiment of the computer-implemented method for a method for using a second learning model for predicting a state of an ophthalmological surgery.

DETAILED DESCRIPTION OF THE FIGURES

Figure 3:
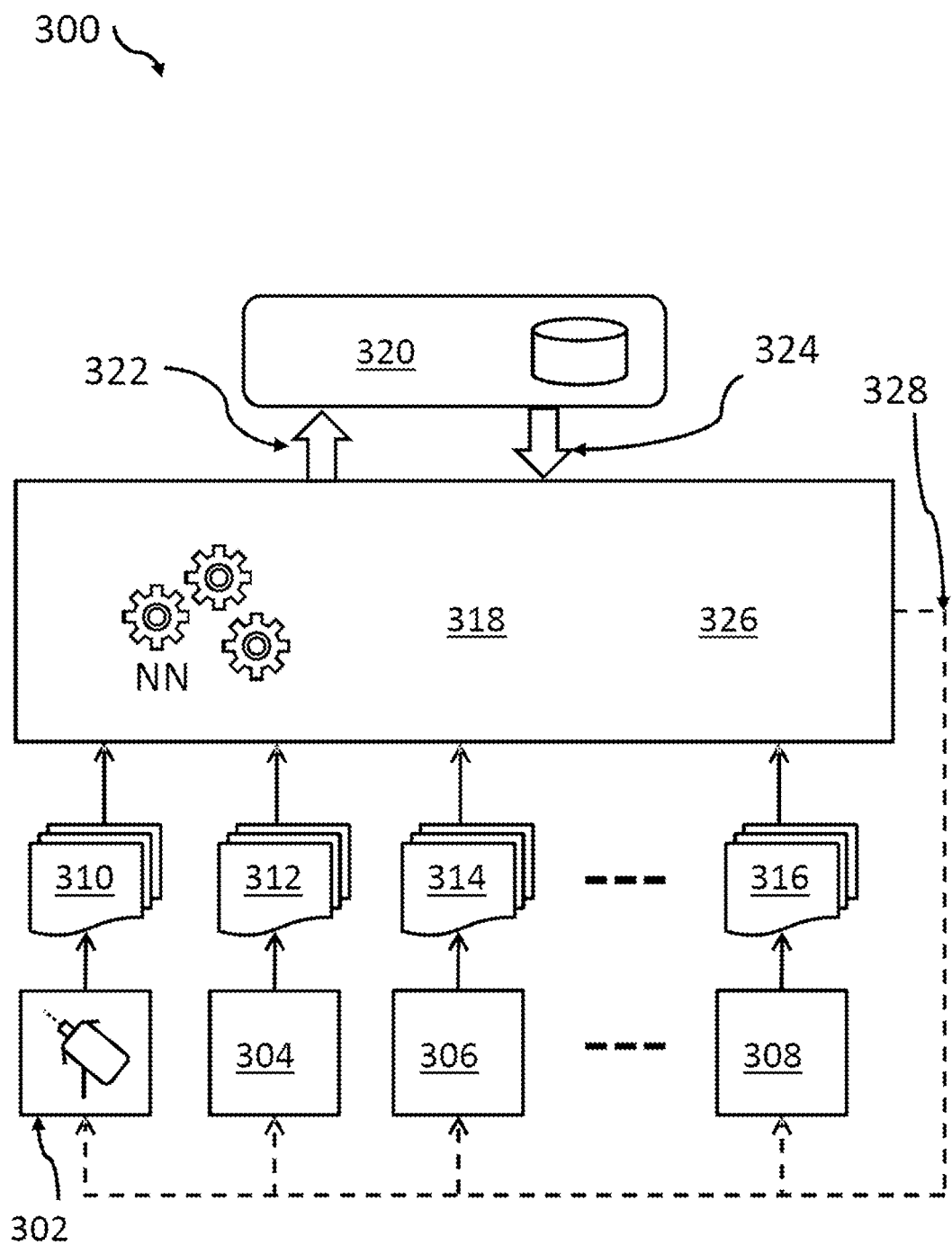
FIG. 3 illustrates an exemplary embodiment of a block diagram of a structure for generating the learning model and for using the learning model.

In the context of this description, conventions, terms and/or expressions should be understood as follows:

The term "assistance function" describes the control of surgery auxiliary devices by means of a control signal, which can be derived from a machine learning system which is able to identify a state of a surgery—e.g., ophthalmological surgery or neurosurgery—or of a surgery phase by means of a trained machine learning system by means of a machine learning model.

The term "surgery auxiliary device" describes surgery-assisting devices such as a surgical microscope, a phaco system, a surgery robot, or an OCT device. However, it is also possible—in the case of specific surgeries—that other or additional surgery auxiliary devices are used. Different device types can be used in the case of the surgical microscope. In ophthalmological surgeries, use is frequently made of those that move in the xy-plane. A movement in the Z-direction is often not required during the surgery. Nevertheless, z-values can also be captured as sensor data in addition to the x- and y-coordinates. It may relate to a robotic microscope in the case of neurosurgery. This is positionable more or less freely in space. The respective axis positions can be captured as sensor data in such a case. Moreover, at least the zoom, focus and light settings of the surgical microscope can be captured as sensor data.

The term "image" or else "digital image"—e.g., from an image sensor of a microscope—in this case describes an image representation of, or the result of generating an amount of data in the form of pixel data from, a physically existing article: by way of example, the interior of an eye in the case of an ophthalmological surgery. More generally, a "digital image" can be understood to be a two-dimensional signal matrix. The individual vectors of the matrix can be adjoined to one another in order thus to generate an input vector for a layer of a CNN. The digital images can also be individual frames of video sequences. Image and digital image or digital image data can be understood to be synonymous in this case.

The term "sensor data" describes measurement data of sensors of a surgery auxiliary device. Here, this may relate to image data, zoom data, focus data, illumination data, position data, flux data, energy data, device activation data, or else time values. In principle, all signals captured by a sensor during a surgery can be used as sensor data.

The term "phaco system" describes a system, by means of which phacoemulsification can be carried out. This is understood to mean the comminution and aspiration of the lens core of an eye by means of a cannula excited by ultrasound and the subsequent aspiration of the fragments by means of an aspiration/irrigation apparatus. This method is frequently applied in the case of a cataract.

The term "state of an ophthalmological surgery" typically describes a phase of the surgery. Various phases, such as preparation phase, capsulorhexis phase, hydrodissection phase, phacoemulsification phase, insertion phase, and sealing phase are discussed elsewhere in this document. The state identification can then lead to the generation of a control signal which represents or facilitates an assistance function for the surgeon. It should moreover be noted that a state can also be derived from a comparison with a reference or standard. To identify anomalies during the progress of the operation, a comparison should be carried out with respect to a standard operation with predefined states. An occurrence of bleeding is independent of the surgery phase in this case and can lead to a corresponding assistance function.

The term "machine learning system" describes a system that is also typically assigned to a method, said system learning from examples. To this end, annotated training data (i.e., training data also containing metadata) is fed to the machine learning system in order to predict output values—output classes in the case of a classification system—that were already set in advance. If the output classes are correctly output with sufficient precision—i.e., an error rate determined in advance—the machine learning system is referred to as trained. Different machine learning systems are known. These include neural networks, convolutional neural networks (CNN) or else recurrent neural networks (RNN). Once the machine learning system has been trained there is a machine learning model which can be described by the parameters of individual functions of the machine learning system. In the case of a neural network, this would be weighting parameters of individual nodes of the neural network.

In principle, the term "machine learning" is a basic term or a basic function from the field of artificial intelligence, wherein statistical methods, for example, are used to give computer systems the ability to "learn". By way of example, certain behavioral patterns within a specific task range are optimized in this case. The methods that are used give trained machine learning systems the ability to analyze data without requiring explicit procedural programming for this purpose. Typically, an NN (neural network) or CNN (convolutional neural network), for example, are examples of systems for machine learning, for forming a network of nodes which act as artificial neurons, and artificial connections between the artificial neurons (so-called links), wherein parameters (e.g., weighting parameters for the links) can be assigned to the artificial links. When training the neural network, the weighting parameter values of the links adjust automatically on the basis of input signals so as to generate a desired result. In the case of supervised learning, the images supplied as input values (training data)—generally (input) data—are supplemented with desired output data (annotations) in order to generate a desired output value (desired class). Considered very generally, mapping of input data onto output data is learned.

The term "neural network" describes a network made of electronically realized nodes with one or more inputs and one or more outputs for carrying out calculation operations. Here, selected nodes are interconnected by means of connections—so-called links or edges. The connections can have certain attributes, for example weighting parameter values, by means of which output values of preceding nodes can be influenced.

Neural networks are typically constructed in a plurality of layers. At least an input layer, a hidden layer, and an output layer are present. In a simple example, image data, for example, can be supplied to the input layer and the output layer can have classification results in respect of the image data. However, typical neural networks have a large number of hidden layers. The way in which the nodes are connected by links depends on the type of the respective neural network. In the present example, the predicted value of the neural learning system can be the sought-after state of the surgery, from which a control signal then is derived.

The term "annotation"—or else "annotated"—denotes a form of metadata, as are used in the context of machine learning for used data—i.e., for example, training data. To this end, training data are provided with metadata—specifically the annotation terms or abbreviated annotations—in the case of supervised learning, said metadata having the desired output class in relation to a certain data record in the case of a classification system. The machine learning system learns by way of examples in this way. Then, in the prediction or inference phase (i.e., in the operative phase following training), a well-trained machine learning system, in response to an input data record, outputs the class that is closest in accordance with the training data.

In the present case, the training data would be annotated with the associated states or phases of the surgery. Optionally, they could also be additionally supplemented with potential control signal annotations. However, the control signals could also be derived directly from the ascertained—i.e., predicted—surgery phases or states.

The term "convolutional neural network" (CNN)—as one example of a classifier/classifier system—describes a class of artificial neural networks that are based on feedforward techniques. They are often used for image analyses using images, or the pixels thereof, as input data. The main components of convolutional neural networks are in this case convolution layers (hence the name) that allow efficient evaluation through parameter sharing. In contrast to the CNN, each pixel of the recorded image would typically be associated with an artificial neuron of the neural network as an input value in a conventional neural network.

The term "support vector machine" (SVM) is used as a classifier for classifying captured data and a regressor for regression analyses. A support vector machine divides a set of objects into classes in such a way that a region around the class boundaries that is as wide as possible remains free from objects; i.e., it is a so-called large margin classifier. An SVM serves for pattern recognition of captured data—e.g., image data following a training phase.

The term "long short-term memory" (LSTM) describes a technique that can substantially contribute to improving the development of artificial intelligence. Error signal descent methods are used when training artificial neural networks. This may fall short in the case of a plurality of deepening layers. The LSTM method solves this problem by virtue of using three types of gate for an LSTM cell for improved memory: an input gate, a forget gate, and an output gate. In this way and in contrast to conventional recurrent neural networks, LSTM facilitates a type of memory of earlier experiences: a long-running short-term memory.

The term "random forest" describes a classification method consisting of a plurality of correlated decision trees. All decision trees have grown under a certain type of randomization during the learning process. For a classification, each tree in this forest can make a decision and the class with the most votes decides the final classification.

The term "AdaBoost" (short for adaptive boost) describes a machine learning meta algorithm. It can be used with other learning algorithms in order to improve the performance. Here, output values of other learning algorithms (of "weak learners") are combined by way of a weighted sum so as to represent the output values of the improved classifier. AdaBoost is adaptable to the extent that incorrectly classified results of preceding learning systems are adapted. In this way, a weak learning system can be altered into a strong learning system.

A detailed description of the figures is given below. It is understood in this case that all of the details and information in the figures are illustrated schematically. Initially, block diagrams are illustrated for exemplary embodiments for the computer-implemented method for generating an assistance function for an ophthalmological surgery and for the method for using a second learning model for predicting a state of an ophthalmological surgery. Further exemplary embodiments or exemplary embodiments for the corresponding systems are described below:

FIG. 1 illustrates a flowchart-like representation of an exemplary embodiment of the computer-implemented method 100 according to the invention for generating an assistance function for an ophthalmological surgery. By way of example, the assistance function can be a surgery phase-dependent switching of device parameters which are used during the surgery. An example would be a variation in the light intensity or in the incoming radiation angle. In addition, anomalies during the course of the surgery can generate (optical or acoustic) warnings and thus a surgery phase-dependent "guidance" (i.e., workflow assistance) for the surgeon—for instance, comparable with GPS functions in a vehicle—can be facilitated.

Examples of types of operation from the field of ophthalmology that are able to be assisted in this way include cataract operations, retinal operations, or corneal transplants. However, the concept presented here is also able to be used in the case of other surgical interventions, for example in neurosurgery.

To this end, the method 100 includes capturing 102 digital image data—i.e., digital images of eyes during a surgery—of a surgical microscope, which were generated by one or more image sensors during an ophthalmological surgery and which are subsequently annotated (106) in manual or (partly) automated fashion. Furthermore, the method 100 includes capturing 104 sensor data of a phaco system, which sensor data were generated during the ophthalmological surgery by a sensor of the phaco system. The sensor data can be annotated (106) in manual or (partly) automatic fashion during or after the actual operation in order to identify individual states or phases of the surgery and use these as metadata for the recorded sensor data. The sensor data could be various pressure levels (e.g., irrigation, aspiration flow), the current ultrasonic power, the ultrasonic pulse mode, or the activation times of the ultrasonic system.

It is helpful if the annotated sensor data and the annotated digital image data from the surgical microscope have synchronized timestamps and the annotations refer in indicative fashion to a state or a phase of the ophthalmological surgery. By way of example, the states could be anomalies that have arisen, clinical pictures that have been identified and/or degrees of severity of the cataract that have been identified. By way of example, the phases could be—particularly in the case of cataract surgeries—a preparation phase, a capsulorhexis phase, a hydrodissection phase, a phacoemulsification phase, an intraocular lens insertion phase and a sealing phase; or, expressed differently, it could relate to the phases of preparation, incision and OVD/BSS application, paracentesis, capsulorhexis, hydrodissection, phacoemulsification, cortex removal, polishing, intraocular lens insertion, OVD removal, wound drying and lens position measurement, irrigation, external OVD application, fixation.

Furthermore, the method 100 includes training 108 the first machine learning system by means of the annotated image data and the annotated sensor data to generate a learning model to predict the state of an ophthalmological surgery and, on the basis thereof, output a control signal which, during a subsequent use of the proposed method, facilitates an assistance function by the trained learning model during a prediction phase of a machine learning system with the learning model generated herein. By way of example, CNN, LSTM, SVM, random forest or AdaBoost are used as possible types for the machine learning system.

FIG. 2 illustrates a flowchart-like representation of an exemplary embodiment of the computer-implemented method 200 for using a second learning model for predicting a state of an ophthalmological surgery. In this context, it is understood that the second learning model can correspond to that which was generated by means of the computer-implemented method 100 according to the invention for generating an assistance function for an ophthalmological surgery.

The method 200 includes capturing 202 digital image data of a surgical microscope during an ophthalmological surgery and capturing 204 sensor data of a phaco system during the ophthalmological surgery. These data are supplied to a second machine learning system which is used to determine 206 a state of an ophthalmological surgery by means of the second machine learning system, which has the trained learning model (cf. method 100) which is adapted to predict a state of an ophthalmological surgery and output 208 a control signal on the basis of the prediction of the state.

Finally, the method 200 includes controlling 210 an assistance function by the control signal during a prediction phase of the second machine learning system during the ophthalmological surgery. Examples of assistance functions that are implemented by the devices and systems used during the surgery (surgical microscope, phaco system, surgery robot and/or OCT system) were already specified further above.

FIG. 3 illustrates an exemplary embodiment of a block diagram for a structure 300 for generating the learning model 320 and for using the learning model 320. During a learning phase for a machine learning system for generating the learning model 320, sensor data (image data and other state data of the devices) are sent from surgery auxiliary devices such as an OCT system 302, a surgical microscope 304, a phaco system 306 and a surgery robot 308 to a joint data processing system 318 and received by the latter. This joint data processing system 318 comprises a machine learning system (the first ML system, neural network, NN) in order to use the received annotated sensor and image data as training data to generate (arrow 322) the learning model 320.

Then, the learning model 320 is used by an assistance system 326 (arrow 324) during a productive phase in order to use the current image and/or sensor data 310, 312, 314, 316 from utilized surgery auxiliary devices as input data during the ophthalmological (or other) surgery for a prediction function ("prediction phase") of the machine learning system 326 to generate a control signal.

It should be noted that this typically relates to different control signals 328 during the training phase and during the prediction phase. Thus, the machine learning model can be trained centrally with a large multiplicity of training data from very different surgeries in order to subsequently implement it decentrally by a different machine learning system of the same type class in a surgery assistance function.

To this end, the control signal 328 is—or a plurality of device-specific control signals are—generated and transmitted to the connected surgery auxiliary or assistance devices—such as an OCT system 302, a surgical microscope 304, a phaco system 306 and a surgery robot 308—in order to implement the surgery assistance function. Since the control signal 328 is only generated in the operative phase, the corresponding control lines for the control signal 328 are illustrated using dashed lines.

Naturally, the machine learning system 318 that is used in the training phase can also be used as machine learning system 326 during the prediction phase.

Figure 4:
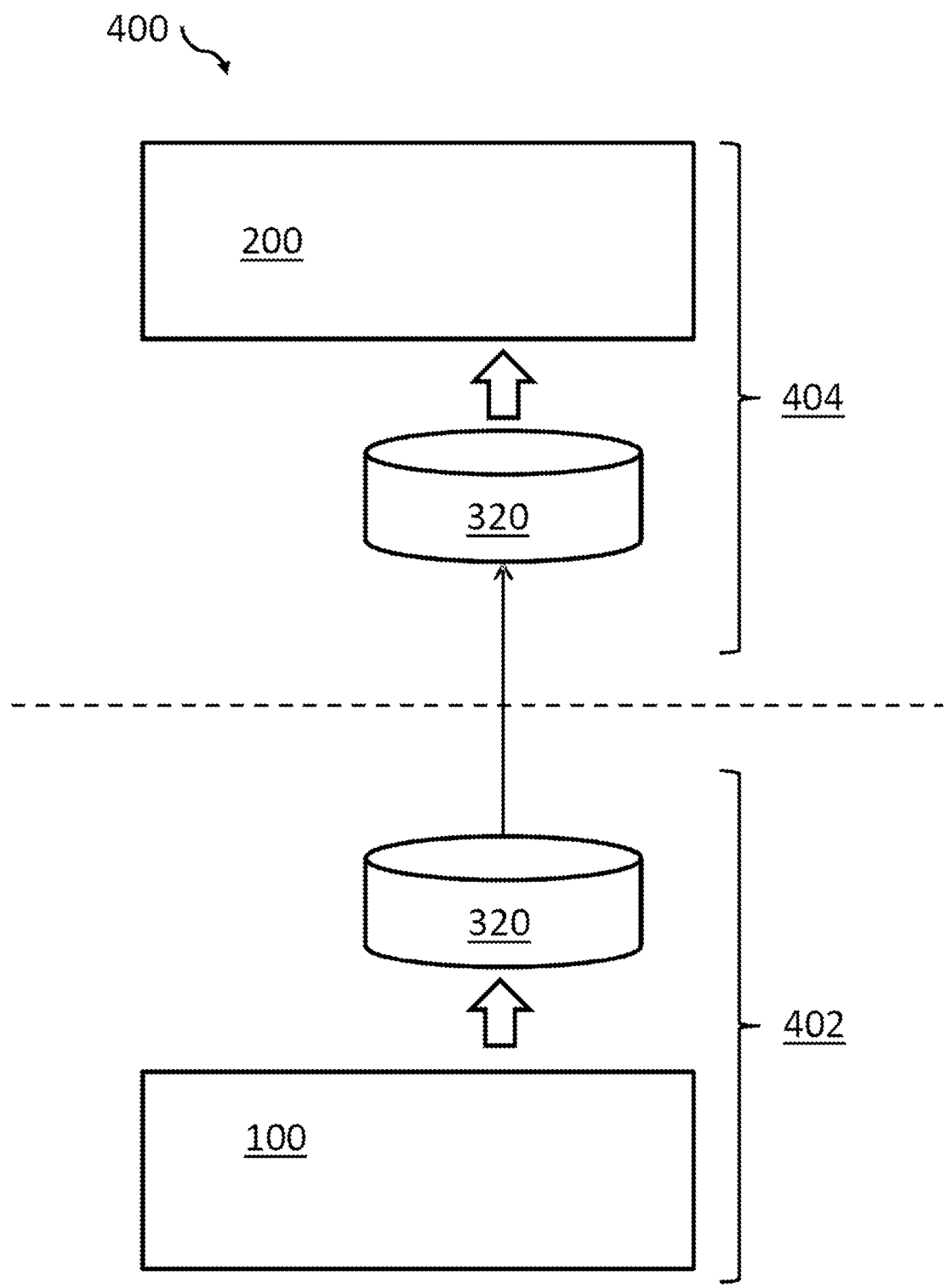
FIG. 4 illustrates a block diagram of generating the learning model and using the learning model in separate systems.

FIG. 4 illustrates a block diagram 400 of generating the learning model and using the learning model in separate systems. Initially, the method 100 (cf. FIG. 1) is used to generate the learning model 320 in a training phase 402. This can be implemented at a central location (e.g., at the device manufacturer or integrator) with the aid of recorded sensor data from a multiplicity of surgeries in order to have available a cross section of many operations by many different surgeons as training data. Alternatively, the method 100 can be used to construct the learning model 320 for a very specific clinic or an individual team of physicians in order to assist a specific surgery technique to the best possible extent.

During subsequent use in an application phase 404, the learning model, generated once, can be used decentrally within the meaning of the "expert in the box" concept. To this end, the learning model is initially exported from the central system in order then to be used decentrally in situ in accordance with the method 200 for using a second learning model for predicting a state of an ophthalmological surgery. Here, the assumption is made that the first (exported) and the second (imported) learning model are identical, i.e., the same parameter values are used in learning models of the same type, i.e., with the same hyperparameters.

Figure 5:
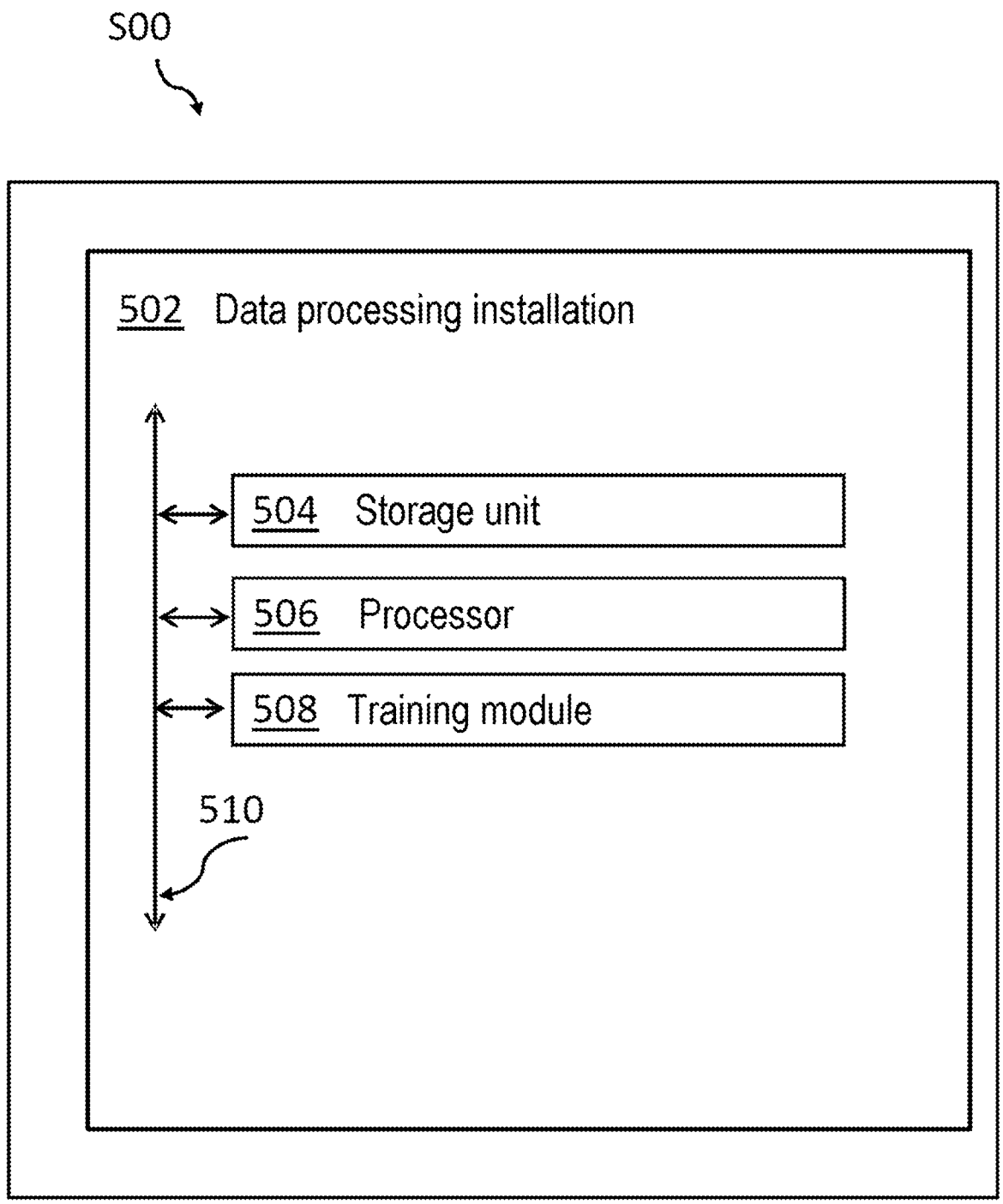
FIG. 5 illustrates an exemplary block diagram for the first machine learning system for generating the assistance function for an ophthalmological surgery.

FIG. 5 illustrates an exemplary block diagram for a first machine learning system 500 for generating the assistance function for an ophthalmological surgery. The machine learning system 500 comprises a storage unit for storing digital image data of a surgical microscope, which were generated during an ophthalmological surgery by an image sensor and which are annotated. The storage unit is also adapted to store sensor data of a phaco system, which were generated during the ophthalmological surgery by a sensor of the phaco system and which are annotated, wherein the annotated sensor data and the annotated digital image data have synchronized timestamps and wherein the annotations refer to states of the ophthalmological surgery. The storage system—or the storage unit 504—can be a joint storage system for storing sensor data from all involved surgery auxiliary devices. This could be, but need not be, a dedicated device. The storage system can also be integrated in one of the involved surgery auxiliary devices.

The machine learning system 500 also comprises a data processing installation 502 (joined-data processing unit), in which the storage unit 504 can be integrated, the latter being connected to a processor 506 in turn, and a training module 508, which is connected to the processor 506. The training module 508 is adapted, together with the processor 506, to train the first machine learning system by means of the annotated image data and the annotated sensor data to generate a learning model to predict a state of the ophthalmological surgery and, on the basis thereof, output a control signal.

Here, the control signal is suitable or designed for facilitating an assistance function in a subsequent use of the machine learning model during a prediction phase of a machine learning system. The control signal can influence the function of the surgery auxiliary devices indirectly (via an approval) or directly (without explicit confirmation by the surgeon). The modules of the system 500 can be interconnected either by electrical signal interchange lines or via the system-internal bus system 510.

Figure 6:
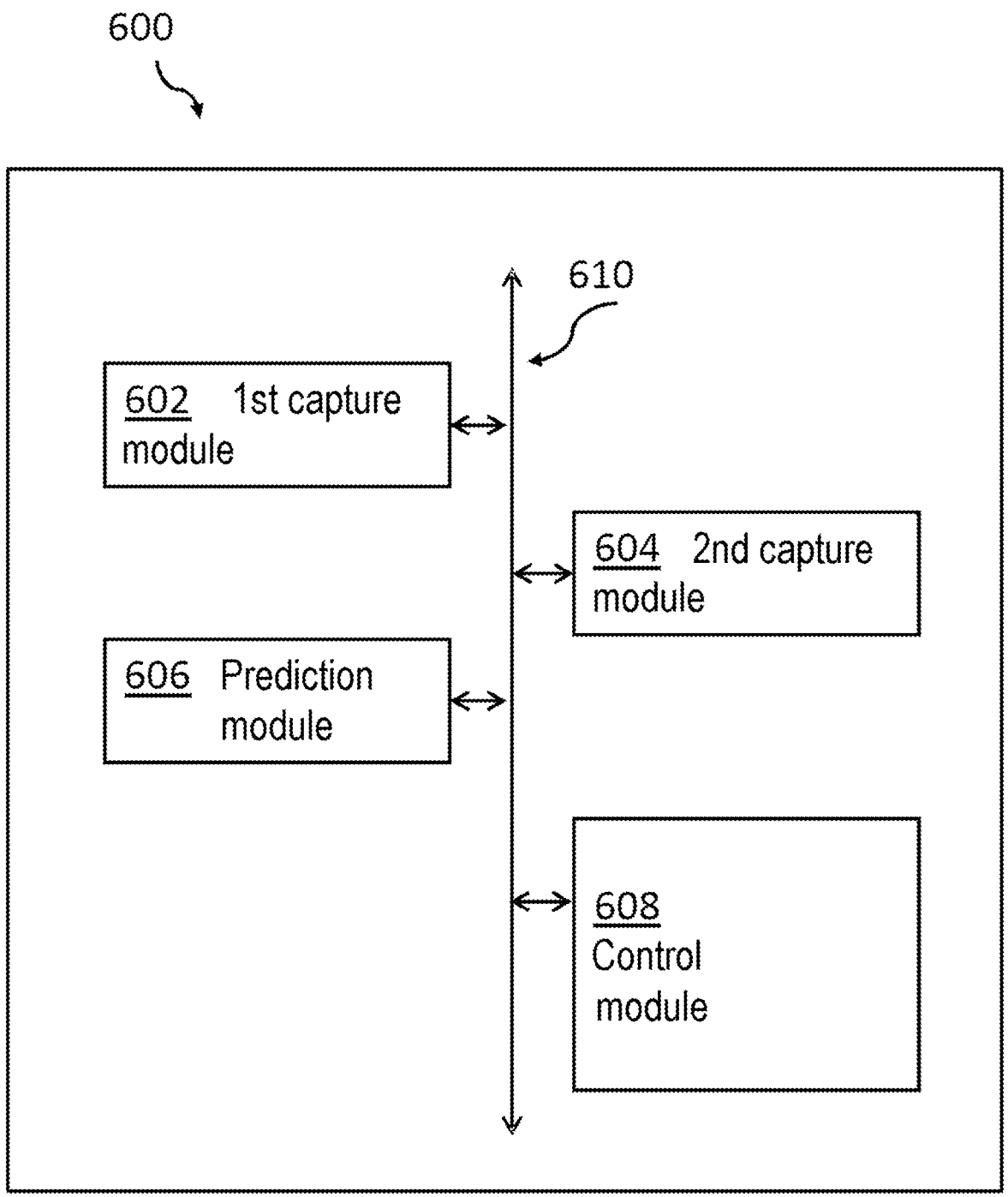
FIG. 6 illustrates the surgery assistance system for using a learning model for predicting a state of an ophthalmological surgery.

FIG. 6 illustrates the surgery assistance system 600 for using a learning model for predicting a state of an ophthalmological surgery and, on the basis thereof, outputting a control signal. The surgery assistance system 600 comprises a first capture module 602 for capturing digital image data of a surgical microscope during an ophthalmological surgery. To this end, the first capture module and the surgery microscope are electrically interconnected for a signal interchange. The surgery assistance system 600 also comprises a second capture module 604 for capturing sensor data of a phaco system during the ophthalmological surgery, wherein the second capture module and the phaco system are electrically connected to a data processing system for signal interchange.

Additionally, the surgery assistance system 600 comprises a prediction module 606 of a second machine learning system (not illustrated) for a prediction of a state of the ophthalmological surgery. The second machine learning system has or uses a trained learning model which by preceding training (potentially on a different learning system of the same type) to predict (in the prediction phase) a state of an ophthalmological surgery, and on the basis thereof, the output of a control signal.

Additionally, a control module 608 which receives the control signal as input signal can be present in the surgery assistance system 600. As a result, the control module 608 is able to control a parameter of one of the ophthalmological surgery devices during a prediction phase of the second machine learning system during the ophthalmological surgery. The modules of the surgery assistance system 600 can be interconnected either by electrical signal interchange lines or via the system-internal bus system 610.

Figure 7:
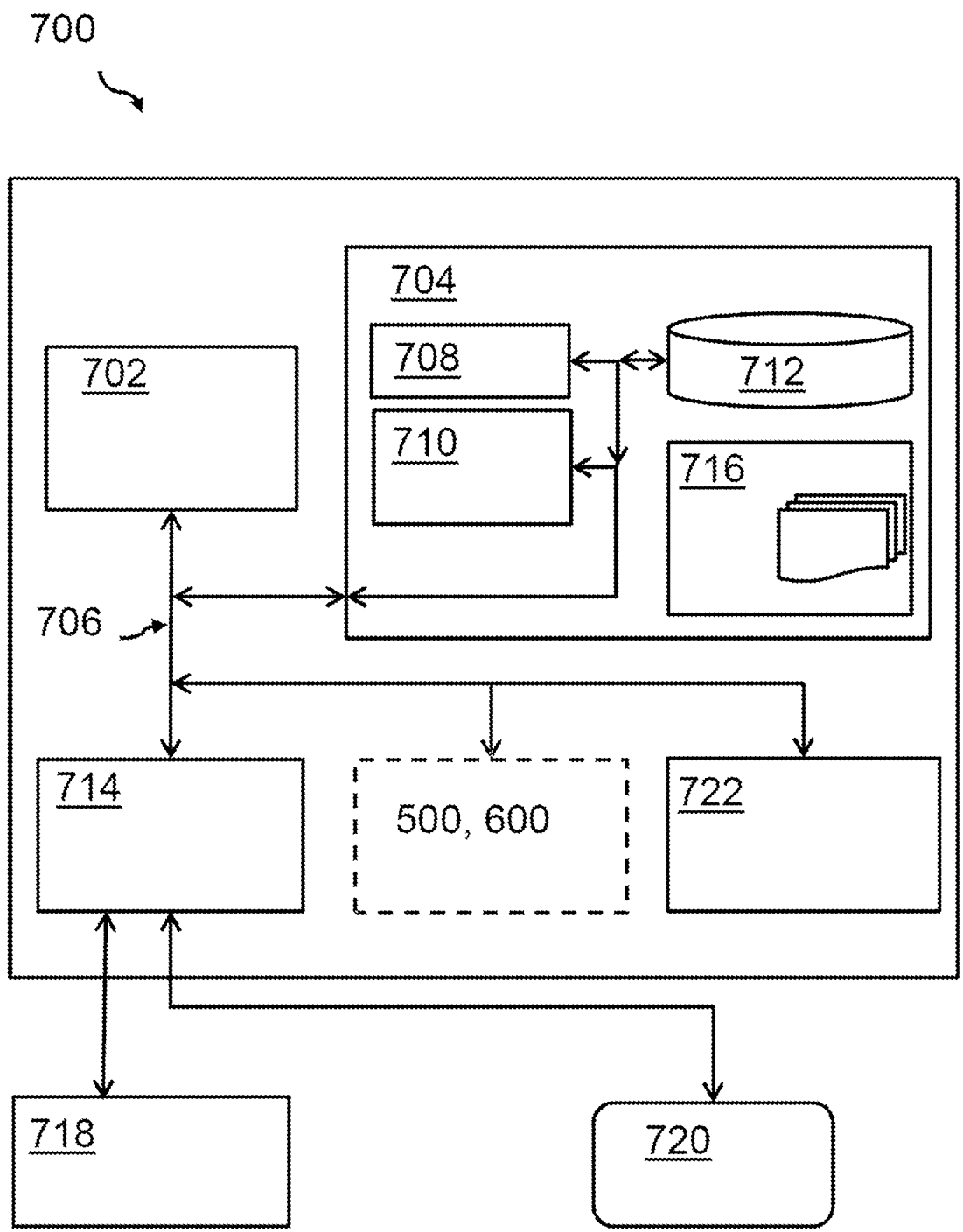
FIG. 7 illustrates a diagram of a computer system which can additionally comprise, in full or in part, the machine learning system as per FIG. 5 or the surgery assistance system as per FIG. 6.

FIG. 7 illustrates a diagram of a computer system which can additionally comprise, in full or in part, the machine learning system 500 as per FIG. 5 or the surgery assistance system 600 as per FIG. 6.

Embodiments of the concept proposed here may in principle be used together with virtually any type of computer, regardless of the platform used therein to store and/or execute program codes. FIG. 7 illustrates by way of example a computer system 700 that is suitable for executing program code according to the method proposed here and may also contain the prediction system in full or in part.

The computer system 700 has a plurality of general-purpose functions. The computer system may in this case be a tablet computer, a laptop/notebook computer, another portable or mobile electronic device, a microprocessor system, a microprocessor-based system, a smartphone, a computer system with specially configured special functions or else a constituent part of a microscope system. The computer system 700 may be configured so as to execute computer system-executable instructions—such as for example program modules—that may be executed in order to implement functions of the concepts proposed here. For this purpose, the program modules may contain routines, programs, objects, components, logic, data structures etc. in order to implement particular tasks or particular abstract data types.

The components of the computer system may have the following: one or more processors or processing units 702, a storage system 704 and a bus system 706 that connects various system components, including the storage system 704, to the processor 702. The computer system 700 typically has a plurality of volatile or non-volatile storage media accessible by the computer system 700. The storage system 704 may store the data and/or instructions (commands) of the storage media in volatile form—such as for example in a RAM (random access memory) 708—in order to be executed by the processor 702. These data and instructions perform one or more functions or steps of the concept proposed here. Further components of the storage system 704 may be a permanent memory (ROM) 710 and a long-term memory 712 in which the program modules and data (reference sign 716) and also workflows may be stored.

The computer system has a number of dedicated apparatuses (keyboard 718, mouse/pointing device (not illustrated), screen 720, etc.) for communication purposes. These dedicated apparatuses may also be combined in a touch-sensitive display. An I/O controller 714, provided separately, ensures a frictionless exchange of data with external devices. A network adapter 722 is available for communication via a local or global network (LAN, WAN, for example via the Internet). The network adapter may be accessed by other components of the computer system 700 via the bus system 706. It is understood in this case, although it is not illustrated, that other apparatuses may also be connected to the computer system 700.

Moreover, at least parts of the first machine learning system 500 for generating the assistance function for an ophthalmological surgery (cf. FIG. 5) and/or of the surgery assistance system 600 for using a learning model for predicting a state of an ophthalmological surgery (cf. FIG. 6) can be connected to the bus system 706.

The description of the various exemplary embodiments of the present invention has been given for the purpose of improved understanding, but does not serve to directly restrict the inventive concept to these exemplary embodiments. A person skilled in the art will himself develop further modifications and variations. The terminology used here has been selected so as to best describe the basic principles of the exemplary embodiments and to make them easily accessible to a person skilled in the art.

The principle proposed here may be embodied both as a system, as a method, combinations thereof and/or as a computer program product. The computer program product may in this case have one (or more) computer-readable storage media that contain computer-readable program instructions in order to prompt a processor or a control system to execute various aspects of the present invention.

Electronic, magnetic, optical, electromagnetic or infrared media or semiconductor systems are used as forwarding medium; for example SSDs (solid state devices/drives as solid state memory), RAM (random access memory) and/or ROM (read-only memory), EEPROM (electrically erasable ROM) or any combination thereof. Propagating electromagnetic waves, electromagnetic waves in waveguides or other transmission media (for example light pulses in optical cables) or electrical signals transmitted in wires also come into consideration as forwarding media.

The computer-readable storage medium may be an embodying apparatus that retains or stores instructions for use by an instruction execution device. The computer-readable program instructions that are described here may also be downloaded onto a corresponding computer system, for example as a (smartphone) app from a service provider via a cable-based connection or a mobile radio network.

The computer-readable program instructions for executing operations of the invention described here may be machine-dependent or machine-independent instructions, microcode, firmware, status-defining data or any source code or object code that is written for example in C++, Java or the like or in conventional procedural programming languages such as for example the programming language "C" or similar programming languages. The computer-readable program instructions may be executed in full by a computer system. In some exemplary embodiments, it may also be electronic circuits such as for example programmable logic circuits, field-programmable gate arrays (FP-GAs) or programmable logic arrays (PLAs) that execute the computer-readable program instructions by using status information of the computer-readable program instructions in order to configure or to customize the electronic circuits according to aspects of the present invention.

The invention proposed here is furthermore illustrated with reference to flowcharts and/or block diagrams of methods, apparatuses (systems) and computer program products according to exemplary embodiments of the invention. It is pointed out that virtually any block of the flowcharts and/or block diagrams may be designed as computer-readable program instructions.

The computer-readable program instructions may be made available to a general-purpose computer, a special computer or a data processing system able to be programmed in another way in order to create a machine such that the instructions that are executed by the processor or the computer or other programmable data processing apparatuses generate means for implementing the functions or procedures that are illustrated in the flowchart and/or block diagrams. These computer-readable program instructions may accordingly also be stored on a computer-readable storage medium.

In this sense, any block in the illustrated flowchart or the block diagrams may represent a module, a segment or portions of instructions that represent several executable instructions for implementing the specific logic function. In some exemplary embodiments, the functions that are illustrated in the individual blocks may be executed in another order, possibly also in parallel.

The illustrated structures, materials, sequences, and equivalents of all of the means and/or steps with associated functions in the claims below are intended to apply all of the structures, materials or sequences as expressed by the claims.

REFERENCE SIGNS

100 Method for generating an assistance function
102 Method step of 100
104 Method step of 100
106 Method step of 100
108 Method step of 100
200 Method for using the learning model
202 Method step of 200
204 Method step of 200
206 Method step of 200
208 Method step of 200
300 Realistic structure of a system for generating a learning model for an assistance function
302 Surgical microscope
304 Phaco system 306 Robot system
308 OCT system
310 Data of the surgical microscope
312 Data of the phaco system
314 Data of the robot system
316 Data of the OCT system
318 First machine learning system
320 Machine learning model
322 Notification arrow
324 Notification arrow
326 Second machine learning system
328 Control signal
402 Training phase
404 Application phase
500 First machine learning system
502 Data processing installation
504 Storage unit
506 Processor
508 Training module
510 System-internal bus system
600 Surgery assistance system
602 First capture module
604 Second capture module
606 Prediction module
608 Control module
610 System-internal bus system
700 Computer system
702 Processor
704 Storage system
706 Bus system
708 RAM
710 ROM
712 Long-term memory
714 I/O controller
716 Program modules, potential data
718 Keyboard
720 Screen
722 Network adapter

The invention claimed is:

1. A computer-implemented method when executed by data processing hardware causes the data processing hardware to perform operations comprising:
capturing digital image data of a surgical microscope, the digital image data generated during an ophthalmological surgery by an image sensor and annotated;
capturing sensor data of a phaco system, the sensor data generated during the ophthalmological surgery by a sensor of the phaco system and annotated;
wherein the annotated sensor data and the annotated digital image data have synchronized timestamps, and wherein the annotations refer in indicative fashion to a state of an ophthalmological surgery, and
training a machine learning system using the annotated image data and the annotated sensor data to generate a learning model to predict a state of an ophthalmological surgery and, on the basis thereof, output a control signal,
wherein the control signal is suitable for facilitating an assistance function in a subsequent use of the trained learning model during a prediction phase of the machine learning system.

2. The method of claim 1, further comprising:
capturing sensor data and/or image data of a surgery robot, the sensor data and/or image data of the surgery robot generated during the ophthalmological surgery and annotated; and
using the annotated sensor data and/or image data of the surgery robot during the training of the machine learning system to generate the learning model.

3. The method of claim 1, further comprising:
capturing optical coherence tomography (OCT) image data of an OCT scanner and/or of a surgery robot, the OCT image data and/or the axis position data of the surgery robot generated during the ophthalmological surgery and annotated; and
using the annotated OCT image data and/or the axis position data during the training of the machine learning system to generate the learning model.

4. The method of claim 1, wherein the predicted the state of the ophthalmological surgery is based on a determination of a surgical instrument characteristic for a respective phase of surgery by applying the machine learning system.

5. The method of claim 1, wherein the control signal is able to be used to control at least one parameter of devices that are used during the ophthalmological surgery.

6. The method of claim 1, wherein the digital image data and the sensor data are captured in time-synchronized fashion in a joint storage system.

7. A method for using a learning model for predicting a state of an ophthalmological surgery, the method comprising:
capturing and annotating digital image data of a surgical microscope during the ophthalmological surgery;
capturing and annotating sensor data of a phaco system during the ophthalmological surgery, the annotated sensor data and the annotated digital image data have synchronized timestamps, and the annotations referring in indicative fashion to a state of an ophthalmological surgery;
training a machine learning system using the annotated digital image data and the annotated sensor data to generate and train a learning model to predict a state of an ophthalmological surgery and, on the basis thereof, output a control signal, the control signal suitable for facilitating an assistance function in a subsequent use of the trained learning model during a prediction phase of the machine learning system;
after training the machine learning system, determining a state of the ophthalmological surgery using the trained machine learning system that has the trained learning model adapted to:
predict an ophthalmological surgery state; and
on the basis of the predicted ophthalmological surgery state, output a control signal; and
controlling an assistance function by the control signal during a prediction phase of the machine learning system during the ophthalmological surgery.

8. The method of claim 7, further comprising:
capturing sensor data and/or image data of a surgery robot, the sensor data and/or image data of the surgery robot generated during the ophthalmological surgery; and
using the sensor data and/or image data of the surgery robot as input for the trained learning model.

9. The method of claim 7, further comprising:
capturing optical coherence tomography (OCT) image data of an OCT scanner and/or of a surgery robot, the OCT image data and/or the axis position data of the surgery robot generated during the ophthalmological surgery; and
using the OCT image data and/or the axis position data of the surgery robot as input for the trained learning model.

10. The method of claim 7, wherein determining the state of the ophthalmological surgery is based on a determination of a surgical instrument characteristic for a respective phase of surgery by applying the machine learning system.

11. The method of claim 7, wherein the control signal is able to be used to control at least one parameter of devices that are used during the ophthalmological surgery.

12. The method of claim 7, wherein the digital image data and the sensor data are captured in time-synchronized fashion in a joint storage system.

13. A surgery assistance system for using a learning model for predicting a state of an ophthalmological surgery and, on the basis thereof, outputting a control signal, wherein the surgery assistance system comprises:
   a first capture module configured to capture digital image data of a surgical microscope during an ophthalmological surgery, wherein the first capture module and the surgical microscope are electrically interconnected for signal interchange;
   a second capture module configured to capture sensor data of a phaco system during the ophthalmological surgery, wherein the second capture module and the phaco system are electrically connected to a data processing system for signal interchange;
   a prediction module of a machine learning system, the prediction module having a trained learning model adapted by preceding training to predict a state of the ophthalmological surgery and, on the basis of the predicted state of the ophthalmological surgery, output a control signal; and
   a control module configured to:
      receive the control signal as an input signal;
      during a prediction phase of the machine learning system during the ophthalmological surgery, control a parameter of a device used during the ophthalmological surgery;
      capture digital image data of a surgical microscope, the digital image data generated during an ophthalmological surgery by an image sensor and annotated;
      capture sensor data of a phaco system, the sensor data generated during the ophthalmological surgery by a sensor of the phaco system and annotated;
      wherein the annotated sensor data and the annotated digital image data have synchronized timestamps, and wherein the annotations refer in indicative fashion to a state of an ophthalmological surgery, and
      train a machine learning system using the annotated image data and the annotated sensor data to generate a learning model to predict a state of an ophthalmological surgery and, on the basis thereof, output a control signal,
      wherein the control signal is suitable for facilitating an assistance function in a subsequent use of the trained learning model during a prediction phase of the machine learning system.

14. The surgery assistance system of claim 13, wherein the preceding training of the learning model comprises training the learning model using the digital image data and/or the sensor data.

15. The surgery assistance system of claim 13, wherein the digital image data and the sensor data are captured in time-synchronized fashion.

16. The surgery assistance system of claim 13, wherein the predicted state of the ophthalmological surgery is based on a determination of a surgical instrument characteristic for a respective phase of surgery by applying the machine learning system.

* * * * *